US00PP31605P3

(12) United States Plant Patent
Bell

(10) Patent No.: US PP31,605 P3
(45) Date of Patent: Mar. 31, 2020

(54) BLUEBERRY PLANT NAMED 'RIDLEY 1602'

(50) Latin Name: *Vaccinium corymbosum*
Varietal Denomination: Ridley 1602

(71) Applicant: Mountain Blue Orchards Pty Ltd., New South Wales (AU)

(72) Inventor: Ridley Bell, New South Wales (AU)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/732,875

(22) Filed: Jan. 9, 2018

(65) Prior Publication Data

US 2018/0288914 P1 Oct. 4, 2018

Related U.S. Application Data

(60) Provisional application No. 62/601,836, filed on Mar. 31, 2017.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

U.S. PATENT DOCUMENTS

| | | | |
|---|---|---|---|
| PP20,806 | P3 | 3/2010 | Abad Alamo et al. |
| PP22,778 | P3 | 6/2012 | Wright et al. |
| PP25,432 | P3 | 4/2015 | Bell |
| PP27,163 | P3 | 9/2016 | Bell |
| 2017/0027092 | P1 | 1/2017 | Bell |

*Primary Examiner* — Susan McCormick Ewoldt
(74) *Attorney, Agent, or Firm* — Plant & Planet Law Firm

(57) ABSTRACT

The new blueberry plant variety 'Ridley 1602' is provided. The variety a selection resulting from seedlings from the controlled pollination of seed parent 'Ridley 1403' (U.S. Plant Pat. No. 25,432) with pollen parent 'Ridley 4609' (U.S. Plant Pat. No. 59,468). The variety can be distinguished by its outstanding features of strong plant growth vigor, upright to semi-upright plant growth habit, low chilling requirement, very early to early time of flowering and fruit ripening, large to very large, sweet, firm, crisp fruit suited to handling, desirable tasting berries and small picking scar.

7 Drawing Sheets

Latin name of the genus and species:
Genus—*Vaccinium.*
Species—*corymbosum.*
Variety denomination: The new blueberry plant claimed is of the variety denominated 'RIDLEY 1602'.

STATEMENT REGARDING FEDERALLY-SPONSORED RESEARCH AND DEVELOPMENT

None.

BACKGROUND OF THE INVENTION

The present invention relates to a new and distinct perennial variety of *Vaccinium* hybrid (Southern Highbush Blueberry), which has been given the variety denomination of 'Ridley 1602'. Its market class is that of a fruiting plant. 'Ridley 1602' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2011 from the controlled pollination of seed parent 'Ridley 1403' (U.S. Plant Pat. No. 25,432) with pollen parent 'Ridley 4609' (U.S. Plant Pat. No. 29,469). The new cultivar was discovered and selected as a single plant within a population of 100 resulting *Vaccinium* hybrid plants from this controlled pollination in 2014 in a commercial field plantation environment at Lindendale, New South Wales, Australia. Selection criteria were a combination of strong plant growth vigor, upright to semi-upright plant growth habit, low chilling requirement, very early to early time of flowering and fruit ripening, large to very large, sweet, firm, crisp fruit suited to handling, desirable tasting berries and small picking scar.

The selection was subsequently evaluated for a number of years at the commercial farms at Lindendale, New South Wales, Australia and Tabulam, New South Wales, Australia.

Asexual reproduction of the new cultivar by cutting propagation since 2014 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

Plants of the new cultivar differ from plants of the seed parent 'Ridley 1403' primarily in more spreading plant growth habit needing more pruning and shaping, smaller sized and more highly flavored fruit whereas the seed parent has a more upright plant growth habit, larger fruit. Plants of the new cultivar differ from plants of the pollen parent 'Ridley 4609' primarily in much earlier flowering and ripening timing and also sweeter fruit whereas the pollen parent has late flowering and ripening timing and less sweet fruit.

The new blueberry variety was designated M14-16-02, and has been planted in replicated trials since 2014.

The new *Vaccinium* hybrid cultivar is a selection resulting from seedlings produced in a breeding programme of *Vaccinium* at Lindendale, NSW, Australia in 2011 from the controlled pollination of seed parent 'Ridley 1403' (U.S. Plant Pat. No. 25,432) with pollen parent 'Ridley 4609'. The new cultivar was discovered and selected as a single plant within a population of 100 resulting *Vaccinium* hybrid plants from this controlled pollination in 2014 in a commercial field plantation environment at Lindendale, New South Wales, Australia. Selection criteria was a combination of strong plant growth vigor, upright to semi-upright plant growth habit, low chilling requirement, very early to early time of flowering and fruit ripening, large to very large, sweet, firm, crisp fruit suited to handling, desirable tasting berries and small picking scar.

The following characteristics of the new cultivar have been repeatedly observed and can be used to distinguish M14-16-02 ('Ridley 1602') as a new and distinct cultivar of *Vaccinium* hybrid plant:

1. Upright to semi-upright bushy plant growth habit
2. Strong to very strong plant growth vigor
3. Large leaf size
4. Very early to early timing of flowering beginning
5. Very early to early timing of fruit ripening
6. Very firm and crisp berry
7. Dry picking scar
8. Large to very large berry size
9. Berry sweetness is very high

BRIEF DESCRIPTION OF THE DRAWINGS

The accompanying photographic illustration shows typical specimens in full color of the foliage and fruit of the new variety 'Ridley 1602' in plants that are approximately 2 years old. The colors are as nearly true as is reasonably possible in a color representation of this type.

Figure 1:
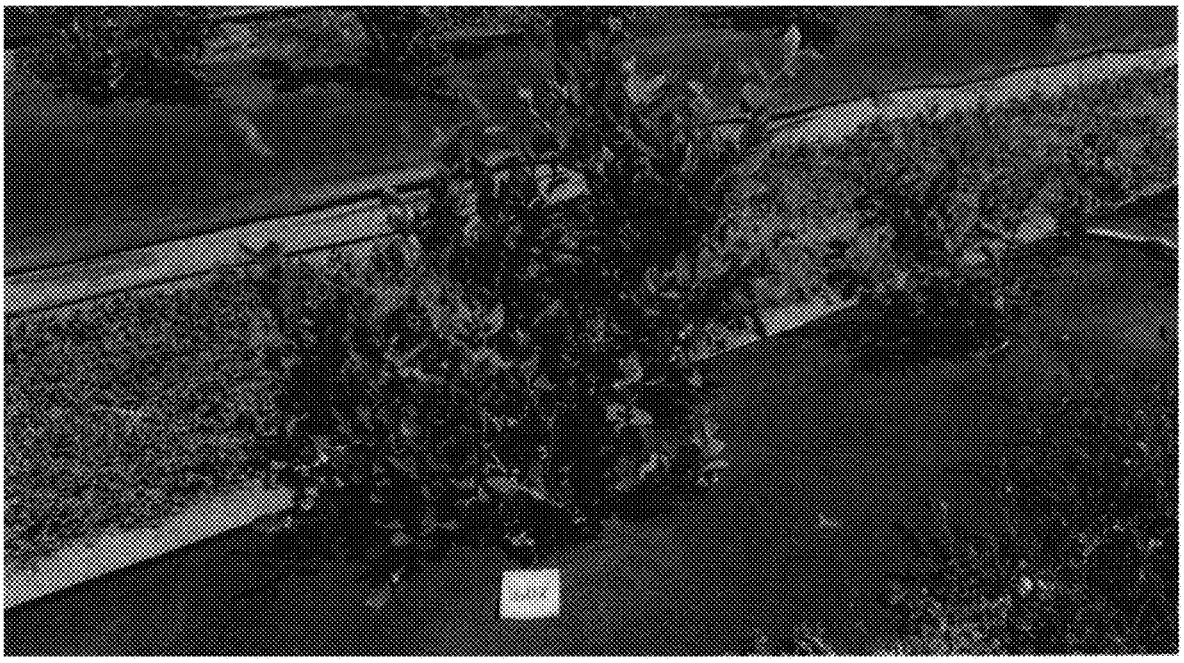
FIG. 1 is a photograph of the new variety 'Ridley 1602', demonstrating the plant's upright growth habit.
Figure 2:
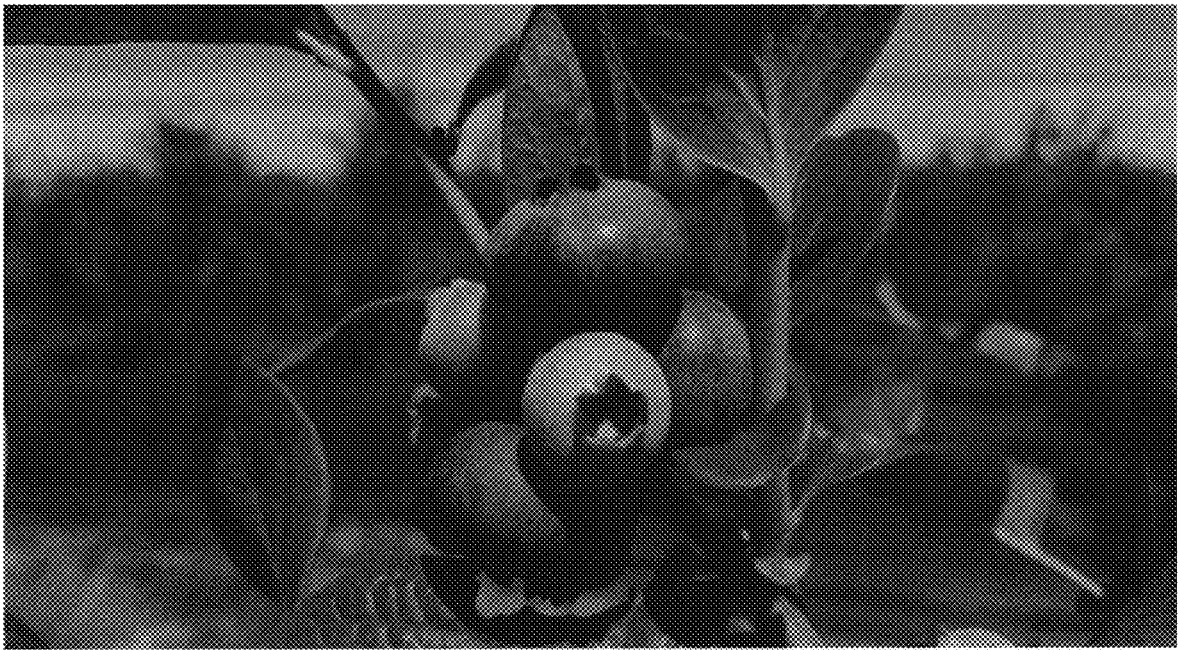
FIG. 2 is a photograph of the fruit of the new variety 'Ridley 1602'.
Figure 3:
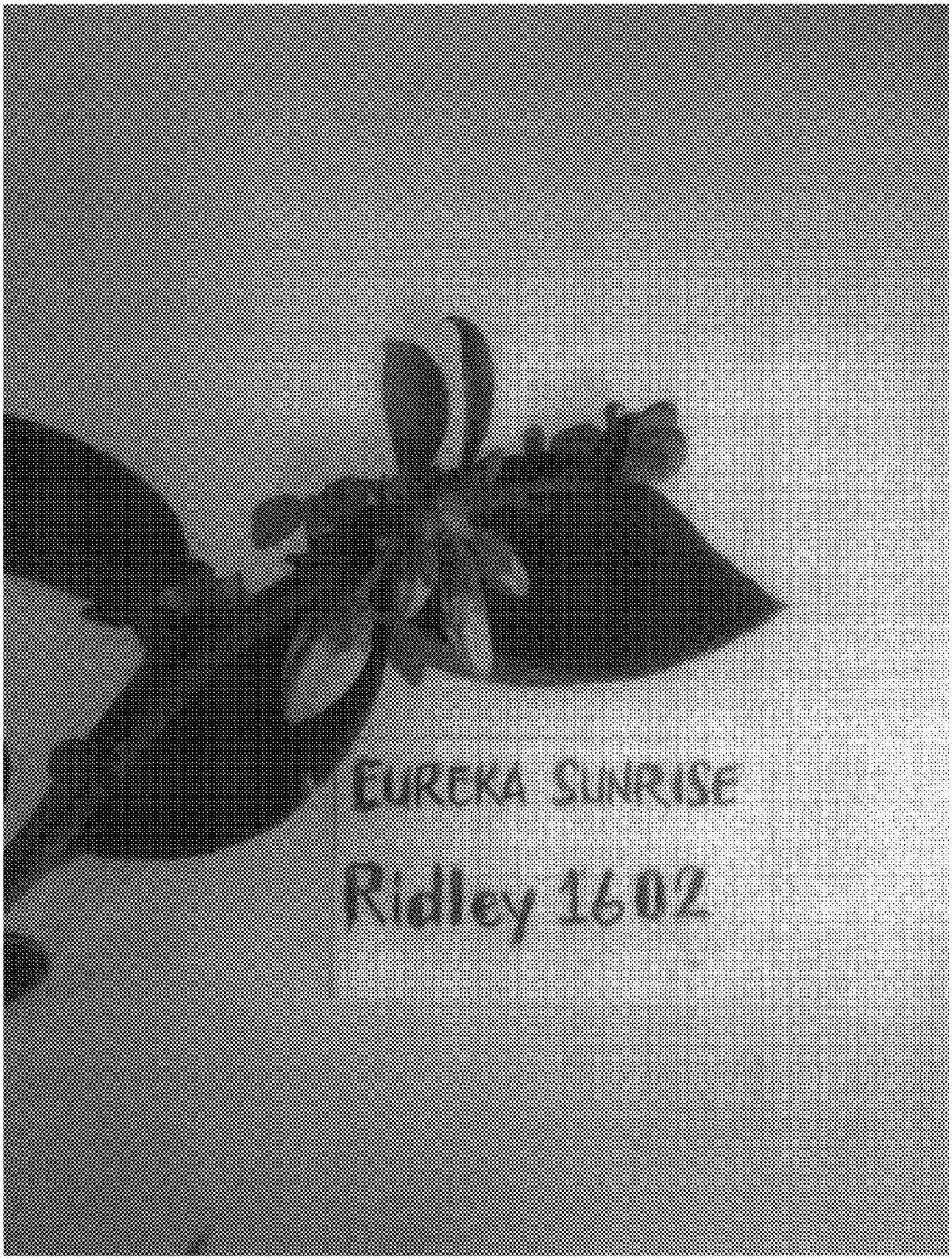
FIG. 3 is a photograph of the flowers of the new variety 'Ridley 1602'.
Figure 4:
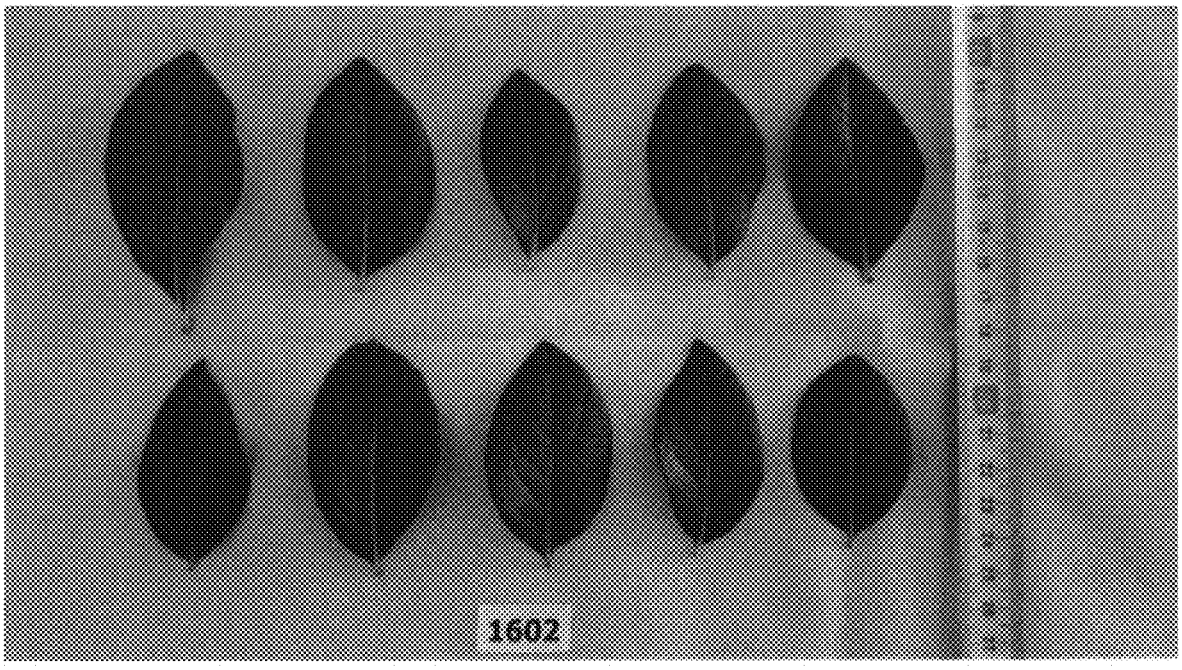
FIG. 4 is a photograph of the leaves of the new variety 'Ridley 1602'.
Figure 5:
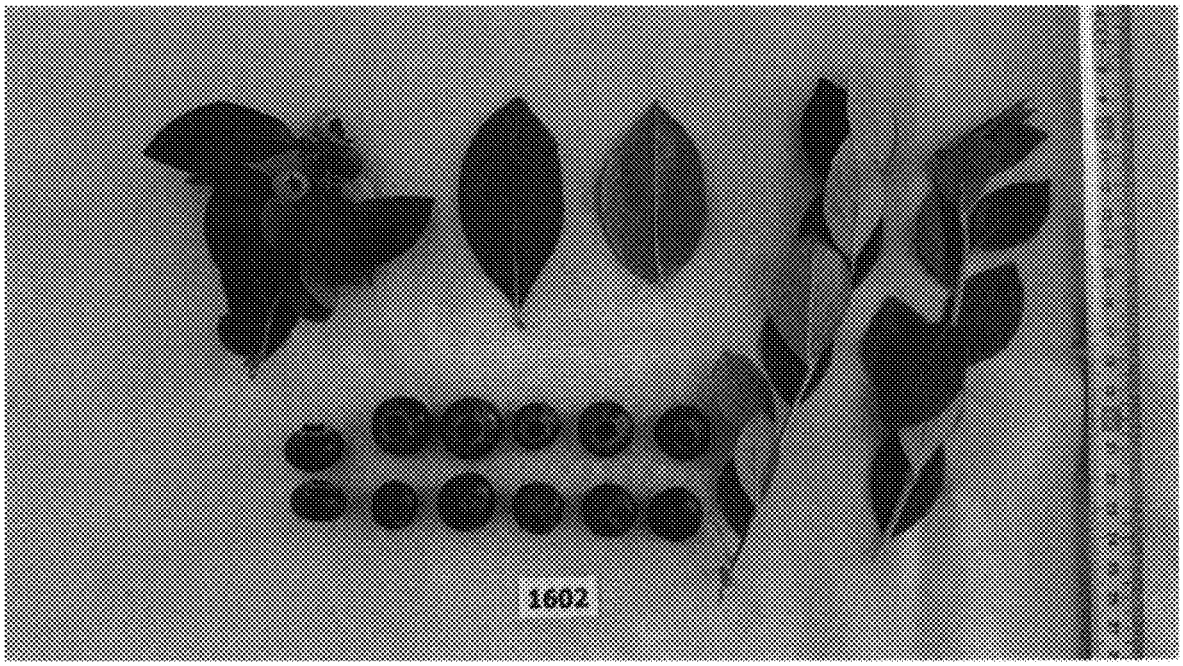
FIG. 5 is a photograph of the leaves, fruit, new shoot and fruit cluster of the new variety 'Ridley 1602'.
Figure 6:
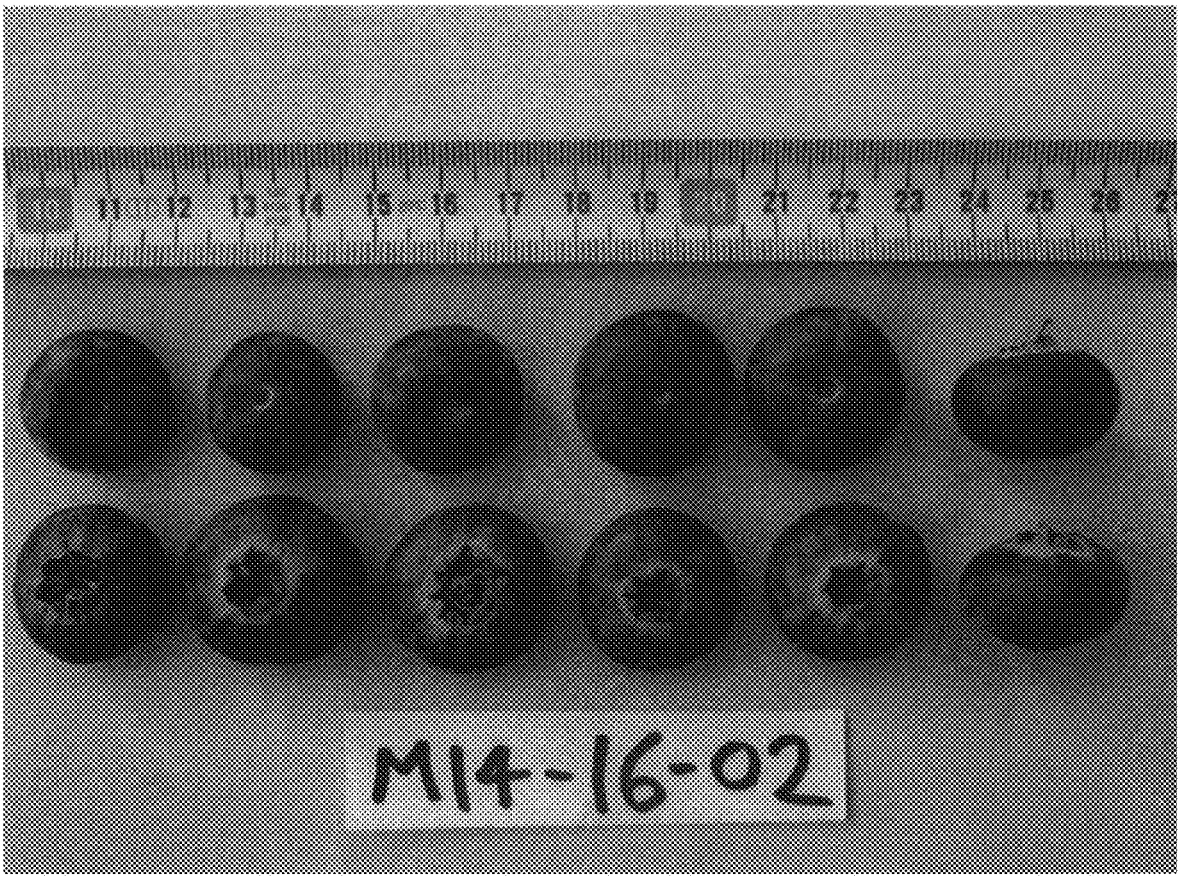
FIG. 6 is a photograph of fruit of the variety 'Ridley 1602'.
Figure 7:
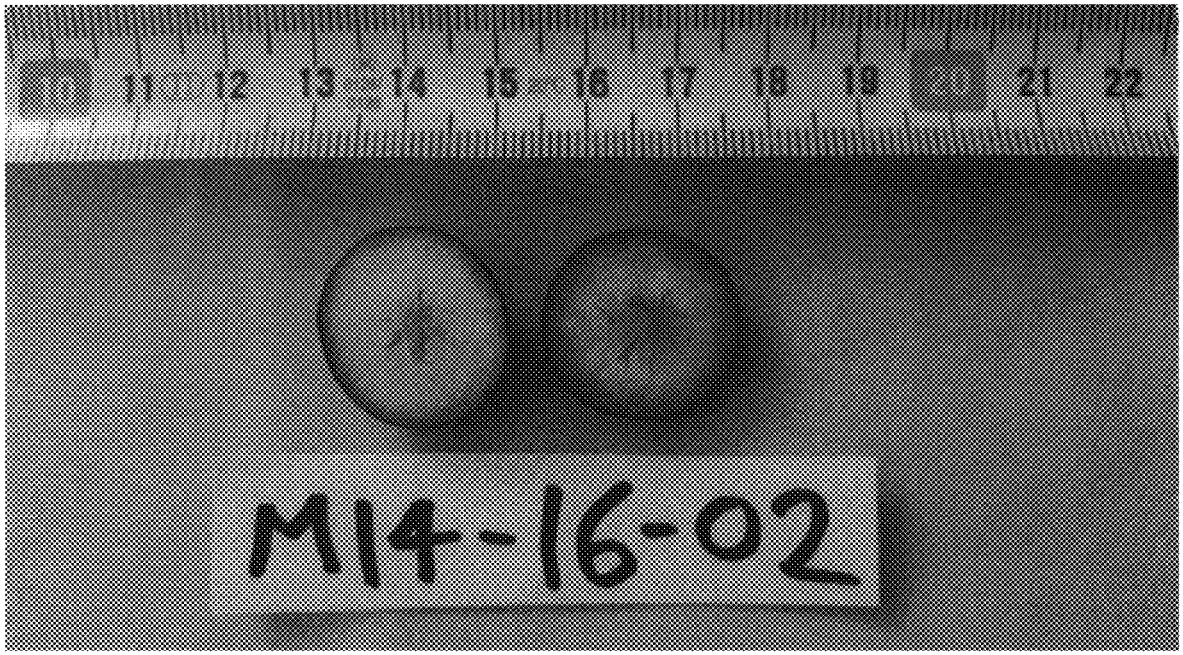
FIG. 7 is a photograph of fruit cross section of the variety 'Ridley 1602'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'Ridley 1602'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Tabulam, New South Wales, Australia. Descriptions of fruit characteristics were made on fruit grown in Tabulam, New South Wales, Australia. Color designations are from Tabulam, New South Wales, Australia.

Color notations are based on *The Royal Horticultural Society Colour Chart*, of The Royal Horticultural Society, London, 2015 edition.

Classification:

a. *Family.*—Ericaceae.
b. *Genus.*—*Vaccinium.*
c. *Species.*—*Corymbosum.*
d. *Common name.*—Southern Highbush Blueberry.

Parentage: Female Parent — 'Ridley 1403' (U.S. Plant Pat. No. 25,432). Male Parent — 'Ridley 4609'.

Market class: A fruiting plant intended for use as fresh fruit for shipping, hand pick, customer pick, machine harvest and processing markets and as a home garden plant.

PLANT

General:

a. *Parentage.*—Female Parent — 'Ridley 1403' (U.S. Plant Pat. No. 25,432).
b. *Male parent.*—'Ridley 4609'.
c. *Plant height.*—1.7 m.
d. *Plant width.*—1.5 m.
e. *Growth habit.*—Upright to semi-upright.
f. *Growth.*—Strong to very strong vigor.
g. *Productivity.*—6 to 7 kg per season from 3-4 year old plants planted at 3.0 m×0.9 m density.
h. *Cold hardiness.*—Has not been grown in all environments including harsh winter environments.
i. *Cold tolerance.*—Cold tolerance is expected to be low.
j. *Chilling requirement.*—Has not been grown in all environments and is typically grown as an evergreen crop where chilling hours are not important. 'Ridley 1602' is classed as 'low chill', typical of Southern Highbush Blueberry varieties with an estimated chilling requirement of 250 hours (not tested).
k. *Tolerance to disease.*—Moderate resistance to root disease (*Phytophthora* spp) and good resistance to blueberry rust.
l. *Leafing.*—Vegetative bud burst is very early when grown as an evergreen in Australia.
m. *Twigginess.*—Low.

STEM

General:

a. *Suckering tendency.*—Plants typically have 5-7 major canes per plant from a base 30 cm in diameter on 6 year old plants.
b. *Mature cane color.*—Color greyed orange 198C.
c. *Mature cane length.*—0.8-1.0 m.
d. *Mature cane width.*—1.2 cm.
e. *Bark texture.*—Medium roughness (typical of species).
f. *Surface texture of new wood.*—Smooth.
g. *Internode length on strong, new shoots.*—20-30 mm.
h. *Fruiting wood.*—To 15 cm in length.

FOLIAGE

General:
a. *Time of beginning of leaf bud burst*.—Very early.
b. *Leaf color* (*top side*).—Yellow green 147A.
c. *Leaf color* (*under side*).—Yellow green 147C.
d. *Leaf arrangement*.—Alternate.
e. *Leaf shape*.—Elliptic.
f. *Leaf margins*.—Entire.
g. *Undulation of margin*.—Weak.
h. *Leaf venation*.—Reticulate.
i. *Leaf apices*.—Acuminate.
j. *Leaf bases*.—Obtuse.
k. *Leaf length*.—60-65 mm.
l. *Leaf width*.—33-40 mm.
m. *Leaf length/width ratio*.—Medium.
n. *Leaf nectaries*.—Absent.
o. *Pubescence of upper side*.—Absent.
p. *Pubescence of lower side*.—Absent.
q. *Cross sectional profile*.—Flat.
r. *Longitudinal profile*.—Straight.
s. *Attitude*.—Semi-upright to horizontal.

Petioles:
a. *Length*.—1.0 to 3.0 mm.
b. *Width*.—2.0 mm.
c. *Color*.—Yellow green 146C-147C.

FLOWERS

General:
a. *Time of beginning of flowering*.—Very early to early (late March-early May to at Lindendale, NSW Australia).
b. *Time of* 50% *anthesis*.—Early July at Lindendale, NSW Australia.
c. *Flower shape*.—Urceolate.
d. *Flower bud density*.—Medium density.
e. *Flower fragrance*.—Weak.

Corolla:
a. *Color*.—White NN155D.
b. *Length*.—9-12 mm.
c. *Width*.—7-9 mm.
d. *Aperture width*.—3-5 mm.
e. *Anthocyanin coloration of corolla*.—Absent, occasional in bud stage.
f. *Corolla ridges*.—Present.
g. *Protrusion of stigma*.—Usually absent.

Inflorescence:
a. *Length*.—40 to 70 mm.
b. *Diameter*.—20-30 mm.
c. *Length of peduncle*.—15 mm.
d. *Surface texture of peduncle*.—Smooth.
e. *Color of peduncle*.—146C.
f. *Length of pedicel*.—7-10 mm.
g. *Surface texture of pedicel*.—Smooth.
h. *Color of pedicel*.—147C.
i. *Number of flowers per cluster*.—9-12.
j. *Flower cluster density*.—Medium.

Calyx (with sepals):
a. *Diameter*.—9-11 mm.
b. *Color* (*sepals*).—Green 138C to yellow green 147C.

Stamen:
a. *Length*.—4-5 mm.
b. *Number per flower*.—Approximately 10.
c. *Filament color*.—Yellow green 144D.

Pistil:
a. *Length*.—10-13 mm.
b. *Style*.—Length — 5-6 mm.
c. *Ovary color* (*exterior*).—Yellow green 144D-147C.

Anther:
a. *Length*.—3.0-3.5 mm.
b. *Number*.—Approximately 10.
c. *Color*.—Grayed orange 167C-D.

Pollen:
a. *Abundance*.—Medium.
b. *Color*.—Grayed orange 167C-D.
c. *Self-compatibility*.—60% fruit set with own pollen in tests at Lindendale, NSW Australia.

FRUIT

General:
a. *Time of fruit ripening*.—Very early to early (early June to mid August at Tabulam, NSW Australia).
b. *Time of* 50% *maturity*.—Early August.
c. *Fruit development period*.—65 days.
d. *Cluster density*.—Medium, 7-10 berries per cluster.
e. *Unripe fruit color*.—Green 138A.
f. *Ripe berry color*.—Black 202A without bloom.
g. *Berry surface wax abundance*.—Strong.
h. *Berry flesh color*.—Greyed green 194C, lightening to 194D, then 193D.
i. *Berry weight*.—4.4-4.8 g.
j. *Berry height from calyx to scar*.—18-20 mm.
k. *Berry diameter*.—24 mm.
l. *Berry shape*.—Oblate.
m. *Fruit stem scar*.—Small (dry).
n. *Sweetness when ripe*.—High to very high.
o. *Firmness when ripe*.—Very firm.
p. *Acidity when ripe*.—Medium to high.
q. *Storage quality*.—Good, lasted 10 weeks at 2 degrees Celsius in tests. Not tested with modified atmosphere storage yet.
r. *Suitability for mechanical harvesting*.—Very firm fruit firmness, strong blush and fruit shape suited to mechanical harvesting. Shake requirement and season compactness not yet tested.
s. *Self-fruitfulness*.—60% fruit set with own pollen in tests at Lindendale, NSW Australia.
t. *Uses*.—Fresh fruit for shipping, customer pick and processing markets and as a home garden plant.

SEED

General:
*Seed abundance in fruit*.—Abundant.
*Seed color*.—Greyed orange 164A.
*Seed dry weight*.—Not yet recorded.
*Seed length*.—1.5-2.0 mm.

COMPARISON BETWEEN COMMERCIAL CULTIVARS

TABLE 1

| Organ | Context | Ridley 1602 | Ridley 4514 (U.S. Plant Pat. No. 27,163P3) | Ridley 1105 (not patented) |
|---|---|---|---|---|
| Plant | vigour | strong to very strong | strong to very strong | strong |

TABLE 1-continued

| Organ | Context | Ridley 1602 | Ridley 4514 (U.S. Plant Pat. No. 27,163P3) | Ridley 1105 (not patented) |
|---|---|---|---|---|
| Plant | growth habit | upright to semi-upright | upright | upright |
| One-year-old shoot | colour | green | green | green |
| One-year-old shoot | length of internode | medium | medium | medium |
| Leaf | length | long | medium to long | long to very long |
| Leaf | width | broad | broad | very broad |
| Leaf | shape | elliptic | elliptic | elliptic |
| Leaf | colour of upper side | green | green | green |
| Leaf | intensity of green colour on upper side (varieties with green leaf colour only) | medium | medium | medium |
| Leaf | margin | entire | entire | entire |
| Flower bud | anthocyanin coloration | weak | weak | weak |
| Flower | shape of corolla | urceolate | urceolate | urceolate |
| Flower | size of corolla tube | medium | medium | medium |
| Flower | anthocyanin colouration of corolla tube | absent or very weak | absent or very weak | absent or very weak |
| Flower | ridges on corolla tube | present | present | present |
| Fruit cluster | density | medium | medium | medium |
| Unripe fruit | intensity of green colour | light | light | light |

TABLE 1-continued

| Organ | Context | Ridley 1602 | Ridley 4514 (U.S. Plant Pat. No. 27,163P3) | Ridley 1105 (not patented) |
|---|---|---|---|---|
| Fruit | size | large to very large | large to very large | large |
| Fruit | shape in longi-tudinal section | oblate | oblate | oblate |
| Fruit | attitude of sepals | erect | erect | erect |
| Fruit | diameter of calyx basin | large to very large | medium to large | medium to large |
| Fruit | depth of calyx basin | deep | deep | medium |
| Fruit | intensity of bloom | strong | strong | strong |
| Fruit | colour of skin | dark blue | dark blue | dark blue |
| Fruit | Firmness | very firm | firm | firm to very firm |
| Fruit | Sweetness | high to very high | medium to high | high |
| Fruit | Acidity | medium to high | weak | medium to high |
| Time of | vegetative bud burst | very early | late | very early |
| Time of | beginning of flowering | very early to early | very early | very early |
| Time of | beginning of fruit ripening | very early to early | early | very early |

The invention claimed is:

1. A new and distinct variety of blueberry plant named 'Ridley 1602', substantially as illustrated and described herein.

* * * * *